United States Patent [19]

Adams

[11] Patent Number: 4,731,556
[45] Date of Patent: Mar. 15, 1988

[54] ELECTRONIC BUBBLE DETECTOR APPARATUS

[76] Inventor: Tello Adams, 8400 141st St. North, Seminole, Fla. 33542

[21] Appl. No.: 29,233

[22] Filed: Mar. 23, 1987

Related U.S. Application Data

[63] Continuation-in-part of Ser. No. 1,901, Jan. 9, 1987.

[51] Int. Cl.[4] .................................... H01L 41/08
[52] U.S. Cl. ............................. 310/338; 310/323; 310/324; 310/328
[58] Field of Search ............... 310/316, 317, 319, 321, 310/322, 323, 324, 338, 339, 800; 73/702, 704, 715–717, 753, 754, 290 V; 340/617–621; 324/61 P, 61 QS; 128/715

[56] References Cited

U.S. PATENT DOCUMENTS

| | | | |
|---|---|---|---|
| 3,603,152 | 9/1971 | Albert et al. | 310/338 X |
| 3,942,049 | 3/1976 | Hyanova et al. | 310/338 |
| 4,019,072 | 4/1977 | Mifune et al. | 310/338 X |
| 4,088,916 | 5/1978 | Weineck et al. | 310/338 |
| 4,176,524 | 12/1979 | Kamiyama | 310/324 X |
| 4,214,484 | 7/1980 | Abts | 310/338 X |
| 4,216,403 | 8/1980 | Krempl et al. | 310/338 |
| 4,304,126 | 12/1981 | Yelke | 310/338 |
| 4,314,242 | 2/1982 | Kuru et al. | 310/338 X |
| 4,391,147 | 7/1983 | Krempl et al. | 310/328 X |
| 4,404,854 | 9/1983 | Krempl et al. | 310/338 X |

FOREIGN PATENT DOCUMENTS 2639164 3/1978 Fed. Rep. of Germany ...... 310/338

*Primary Examiner*—Mark O. Budd

[57] ABSTRACT

An oscillator utilizes a piezo-electric transducer as a frequency determining element. The transducer, when unloaded, has a resonant frequency which determines the oscillation frequency and exhibits a preternined level of amplitude excursion. A clamping mechanism detachably couples the transducer into engagement with a conduit through which fluid flows. This action increases the loading of the transducer and produces a change of resonant frequency, causing the oscillator frequency to change, and also causing the level of amplitude excursion to change. The amount of oscillator frequency change and the change in excursion level have respective values when the fluid flowing in the conduit past the transducer is bubble free which differ from the respective values when the fluid contains bubbles. Circuitry responsive to the changing amplitude values produces an output signal when a selected one of the bubble free and bubble containing conditions is detected. Apparatus responsive to the output signal produces a visual equivalent thereof.

10 Claims, 16 Drawing Figures

3rd SIGNAL

4th SIGNAL

1st SIGNAL

2nd SIGNAL

5th SIGNAL

6th SIGNAL

6th SIGNAL (UPPER TRACE)
7th SIGNAL (LOWER TRACE)

6th SIGNAL (UPPER TRACE)
8th SIGNAL (LOWER TRACE)

ELECTRONIC BUBBLE DETECTOR APPARATUS

CROSS REFERENCE TO COPENDING APPLICATION

This application is a continuation-in-part of copending application entitled "Electronic Bubble Detector Apparatus, Ser. No. 001901, filed Jan. 9, 1987.

BACKGROUND OF THE INVENTION

It is often necessary as for example in air conditioning and heating systems to eliminate or prevent the formation of bubbles such as gas bubbles in fluids flowing through pipes and other conduits. Accordingly visual displays such as sight glasses are employed to enable fluid flow to be monitored. However, depending upon the type of fluid and type of conduit, such displays cannot be or are not always used. Moreover, even when such displays are used, periodic visual inspection by trained observers is necessary, and, even under these conditions, dangerous bubble conditions can develop between inspection periods and thus be undetected. The invention disclosed in the aforementioned copending application is directed toward electronic apparatus which will automatically and continuously detect the presence or absence of bubbles in fluid flows and which will produce an electrical signal which can be used to sound an alarm, operate control devices or initiate other immediate corrective action. Since the apparatus, once installed, can be operated remotely, it can be used in radioactive and other environments in which operator access is dangerous or forbidden.

The present invention is directed toward apparatus of the same type, but includes an arrangement for providing a visual display which produces a visual effect similar to that experienced when a mechanical sight glass permanently installed in a conduit or pipe is examined. The present invention also utilizes a unique clamping arrangement for detachably coupling the transducer to the conduit or pipe.

SUMMARY OF THE INVENTION

In accordance with the principles of the invention, electronic apparatus is adapted for use with any conduit through which fluid flows to determine whether or not bubbles are present in the fluid.

The apparatus utilizes an oscillator which employs a piezo-electric transducer as a frequency determining element. The transducer, when free of any load, has a resonant frequency which determines the oscillator frequency, and also exhibits a pretermined level of amplitude excursion. When the transducer is placed in engagement with the outer surface of the conduit, the mass flow of the fluid past the transducer creates a load thereon. Consequently, the resonant frequency of the transducer changes as does its level of amplitude excursion. The amount of oscillator frequency change and the amount of change in excursion level have respective values when the fluid flow past the transducer is bubble free which differ from the respective values when this fluid flow contains bubbles.

Clamping means secures the transducer to the conduit and includes a box having a wall with an inner surface adjacent the transducer and an outer surface adjacent the conduit. This means can accommodate a range of different conduit diameters. As long as the conduit diameter falls within this range, this means is adapted to automatically center the transducer so that it is always adjacent the center of the conduit, thereby establishing optimum mechanical coupling between transducer and conduit.

Means responsive to the changing values of amplitude level produces a signal when bubble containing flow is present, or, alternatively, when the flow is bubble free. When the signal produced indicates the presence of bubbles, this signal can be used to provide a visual display similar to that experienced when a mechanical sight glass permanently installed in the conduit displays the presence of bubbles.

The foregoing and other objects and advantages of this invention as well as other objects and advantages thereof will either be explained or will become apparent to those skilled in the art when this specification is studied in conjunction with the accompanying drawings and specific description of preferred embodiments which follow.

DETAILED DESCRIPTION OF PREFERRED EMBODIMENTS

Figure 1:
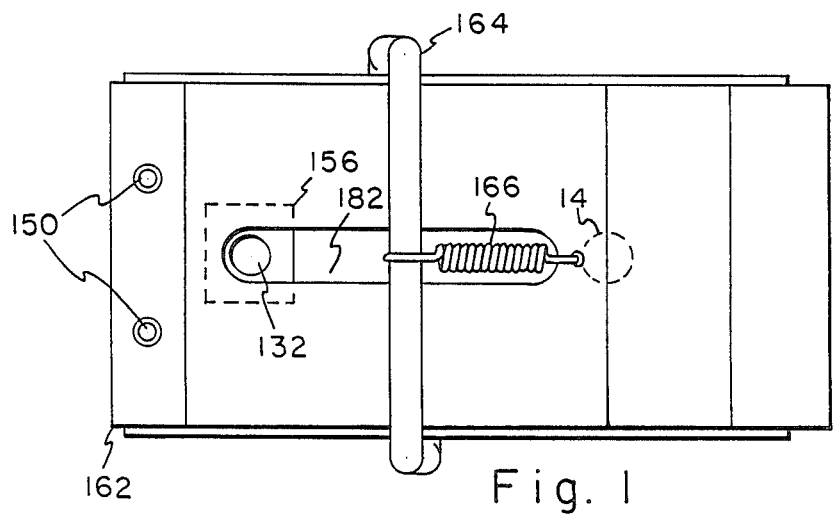
FIGS. 1-6 show various views of clamping means employed in the invention for coupling a piezo-electric transducer with the outer surface of a pipe.
Figure 2:
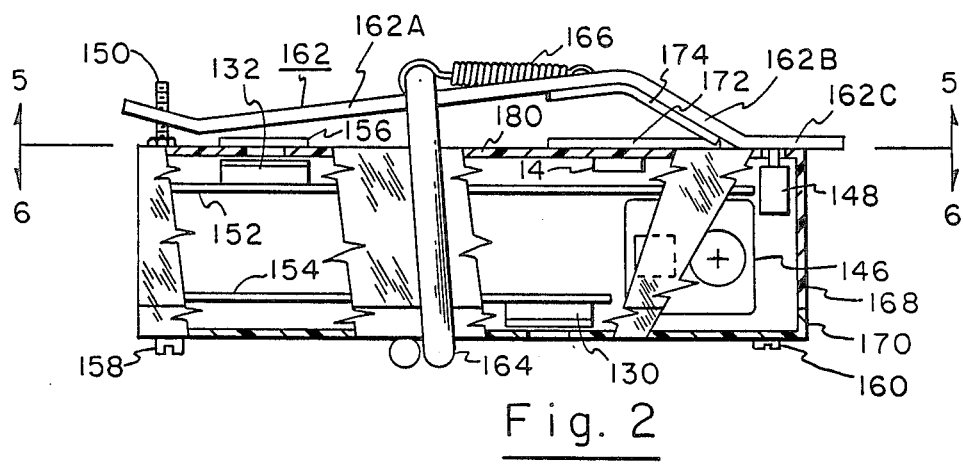
Figure 3:
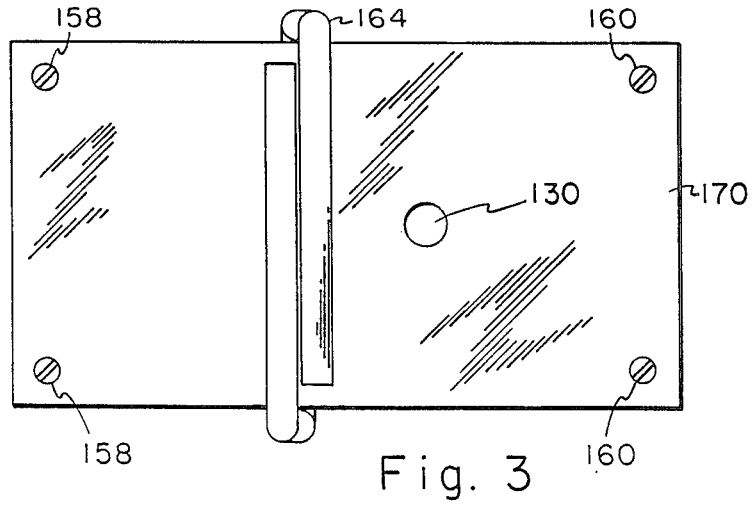
Figure 5:
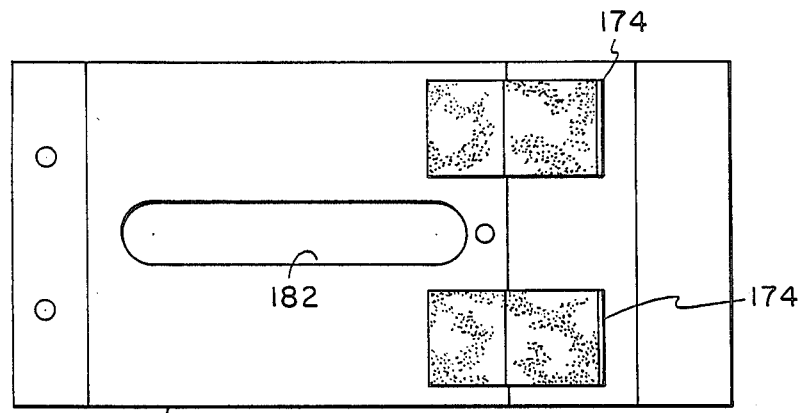
Figure 6:
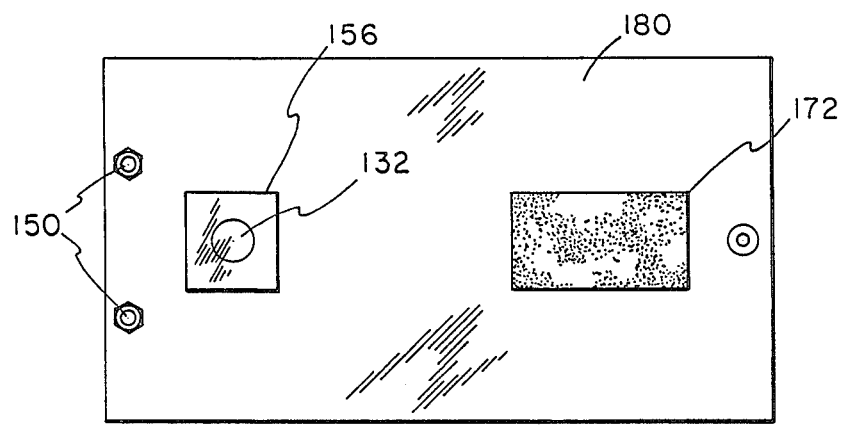
Figure 4:
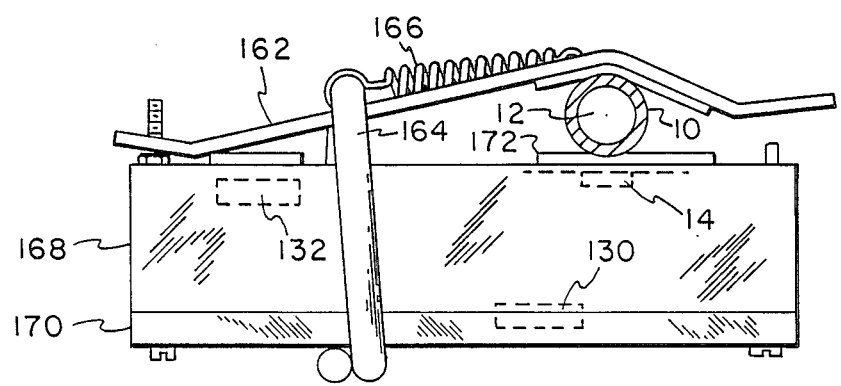

Referring first to FIGS. 1-6, a hollow rectangular box or container 168 has a removable flat bottom cover 170 held in place by retainers 158 and screws 160 and also has an integral top cover 180. A clamp plate 162 is positioned on top of the container and is secured to and is pivotable about two spaced vertical pins 150 which are secured to cover 180. The plate 162 has a major portion 162A which is inclined upwards from pins 150 and terminates in a minor portion 162B which inclines downwardly therefrom. Portion 162B has a flat horizontal extension 162C. The plate also has a longitudinally extending slot 182 which extends along the longitudinal center line thereof. A retaining ring 164 encircles the box and clamp plate and is slidable back and forth toward and away from pins 150. A tension spring 166 is secured at one end to portion 162A adjacent portion 162B and is secured at the other end to ring 164. A soft pad 172, for example a neoprene pad, is glued or otherwise bonded to the outer surface of cover 180. Additional soft pads are likewise secured to the bottom surface of adjacent areas of portions 162A and 162B on opposite sides of pad 172. A piezo-electric transducer 14 is bonded on one surface to the surface of cover 180 remote from the top cover. The included angle between portions 162A and 162B, the vertex line of this angle and the position of transducer 14 are so related that the transducer is always properly positioned with respect to the conduit even though the outer diameters of the conduit can vary over a wide range. When the ring 164 is slid toward pins 150 [and if necessary, locked in position against retainers 158], the clamp plate can be pivoted upwardly about the pins, and the box can be moved until a pipe or conduit is disposed on top of pad 172 and extends along the region common to both portion 162A and 162B. When the ring is released, spring 166 pulls the ring toward the conduit, pulling the clamp plate downwardly and clamping the pipe in position.

The transducer and pipe are thus automatically centered with respect to each other. The pads establish a high friction engagement so that the structure will remain in proper position on the pipe or conduit without additional or external support. The pad 172 also establishes good acoustical contact between pipe and transducer even when the pipe surface is rough or irregular.

A liquid crystal display unit 130 is secured to the bottom of the box and can be viewed through the opening in the cover 170 and a second like unit 132 is secured to the inner surface of the top cover and can be viewed through the slot 182. The box also contains a battery 146, the circuitry, which is on two printed circuit boards, and an on-off switch 148. The switch has a plunger which, when depressed, is in the off position. When the plunger is spring biased, it is in an extended position which is the on position. Consequently, when the clamp plate engages a pipe, portion 162C is spaced above the switch and it is in the on position. When a pipe is not engaged, portion 162C bears against the plunger and depresses it whereby the switch is in the off position.

The transducer 14 can be a thin flat disc having, for example, a diameter of 0.25 inches and a thickness of 0.08 inches. Transducers, depending upon their geometry, have resonant frequencies which differ, depending upon the mode of operation. Transducer 14 can resonate in the radial mode, across the disc, whereby the amplitude excursions of the disc cause it to elongate and contract in the plane of the disc, and can also resonate in the axial mode, through the disc, whereby the amplitude excursions of the disc cause it to elongate and contract in a direction perpendicular to the plane of the disc. The radial mode amplitude excursions were found to be sufficient for use with the circuit shown in FIGS. 5 and 6. The particular transducer described above was found to have a resonant frequency [unloaded] of about 320 kilohertz.

Figure 7:
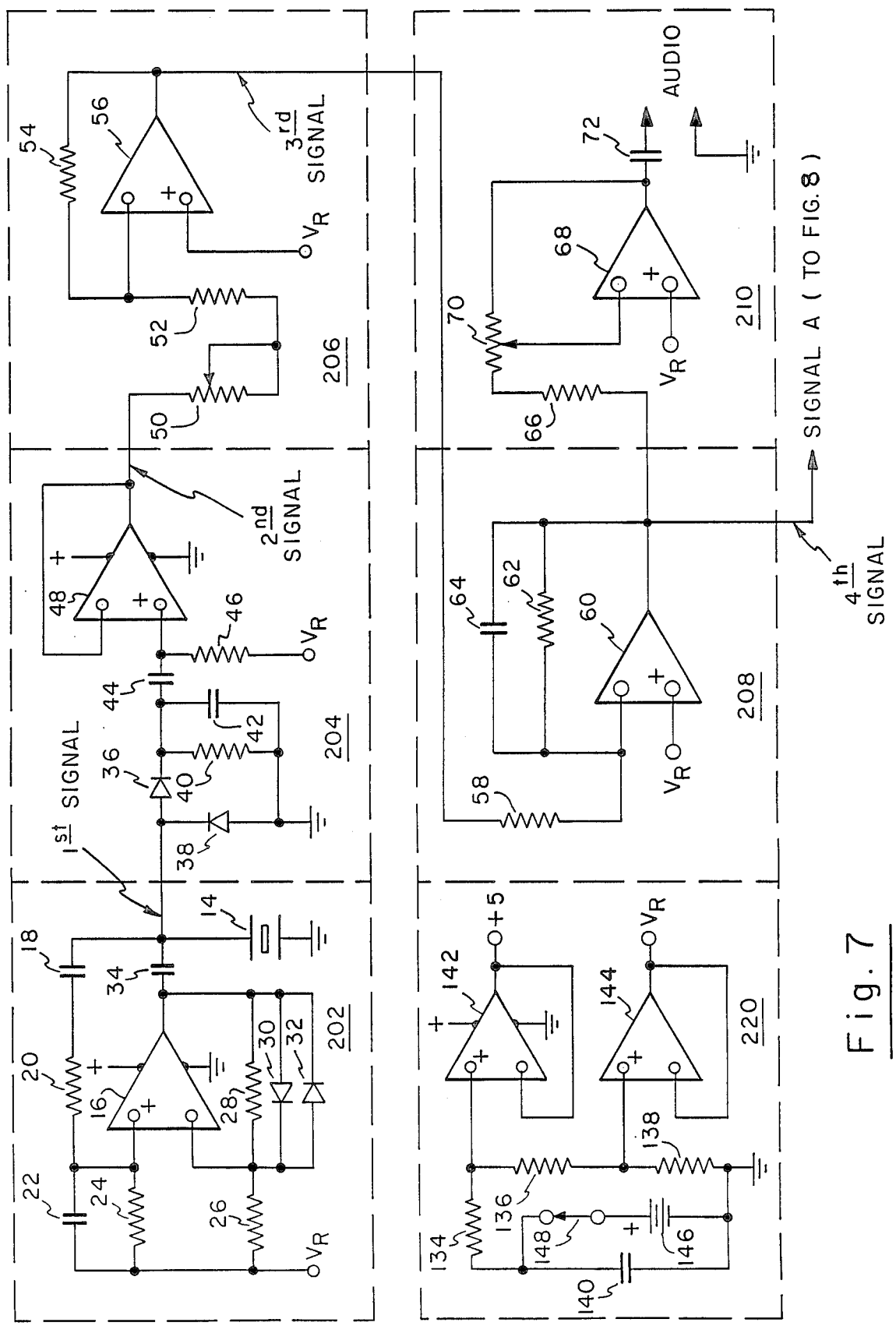
FIGS. 7-8 are circuit diagrams of the circuitry employed in the invention.
Figure 8:
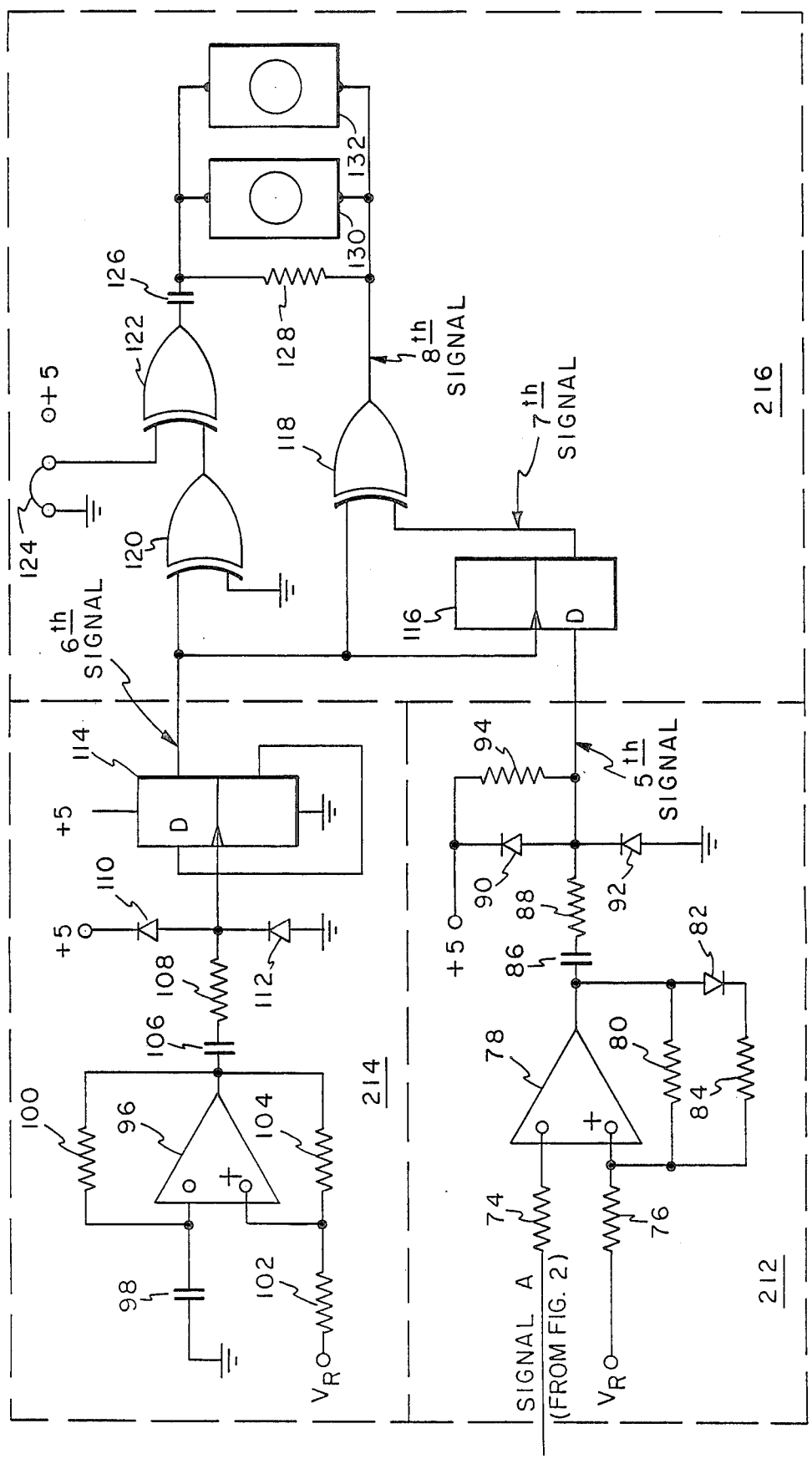
Figure 11:
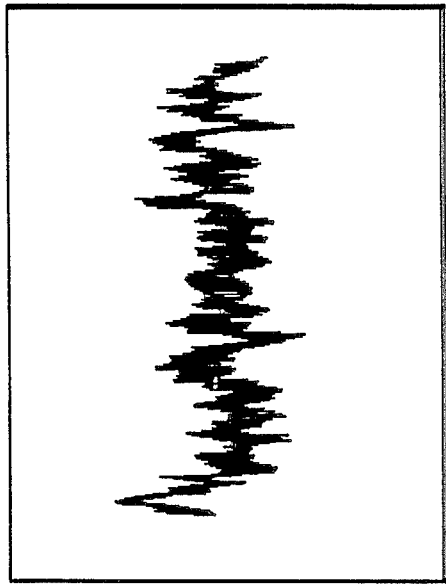
FIGS. 9-16 illustrates waveforms of the various signals produced in the circuitry shown in FIGS. 4 and 5.
Figure 12:
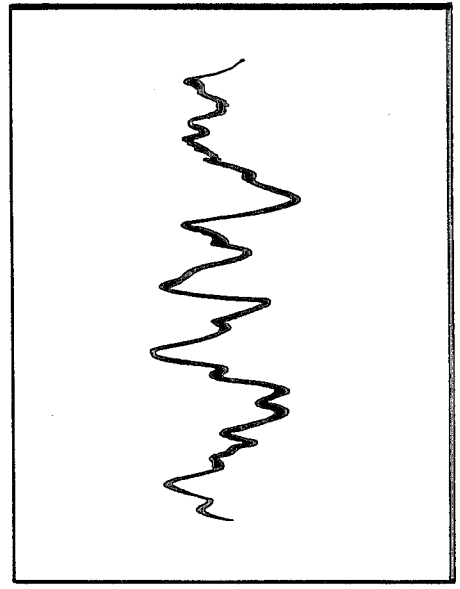
Figure 9:
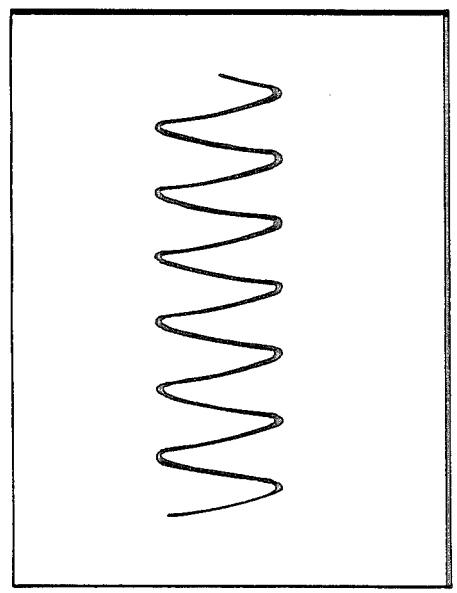
Figure 10:
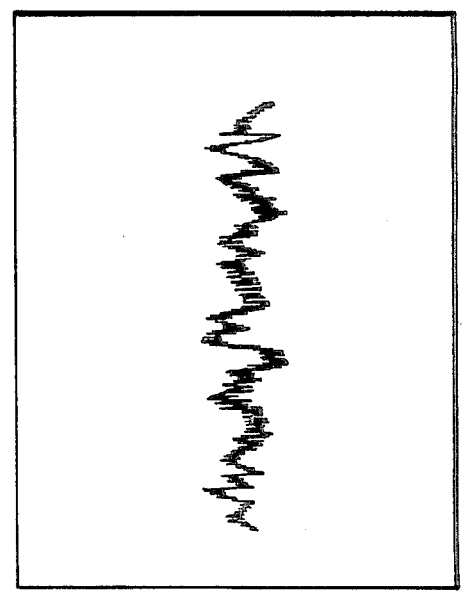

Referring now to FIGS. 7 and 8, an oscillator 202 using transducer 14 yields a first signal having the waveform shown in FIG. 9. The first signal is at carrier frequency [the oscillator frequency] which in the presence of bubbles in the fluid flow is amplitude modulated by the amplitude excursions of the loaded transducer. This first signal is supplied to the input of a signal detector and filter stage 204. Stage 204 removes most of the carrier frequency component from the first signal and derives therefrom a second signal having the waveform shown in FIG. 10. The second signal consists primarily of an alternating current component, the frequency and amplitude of which is proportional to the amplitude excursions of the transducer caused by the presence of bubbles. The second signal is supplied to the input of stage 206 wherein it is amplified, thereby producing a third signal having the waveform shown in FIG. 11. The third signal also contains an unwanted carrier frequency component. The third signal is supplied to the input of stage 208 whigh is a low pass filter with gain. Stage 208 removes the unwanted carrier frequency component from the third signal and derives therefrom a fourth signal having the waveform shown in FIG. 12 which contains only the alternating current component and thus identifies uniquely the presence of bubbles in the fluid. When the fourth signal has a zero value, this zero value identifies uniquely the absence of bubbles in the fluid. The fourth signal is then supplied to a variable gain buffer stage 210 which generates an output signal capable of providing an input to head phones or other audio reproduction device. The sound produced resembles the bubbling noise produced when a child blows bubbles from a bubble pipe dipped into a suitable liquid. No sounds are produced when the liquid in the conduit is bubble free.

Figure 13:
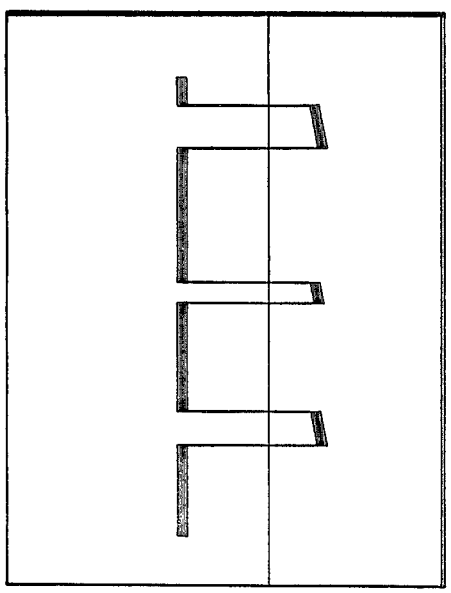

The fourth signal is also supplied as an input to a threshold detector and level converter stage 212. Stage 212 produces a variable pulse width digital signal with alternate positive going and negative going pulses wherein the pulse widths and spaces between pulses are proportional to the duration of the alternating current component excursions beyond preset positive and negative thresholds. This signal is then limited to standard digital logic voltages, thereby producing a fifth signal having the waveform shown in FIG. 13.

Figure 14:
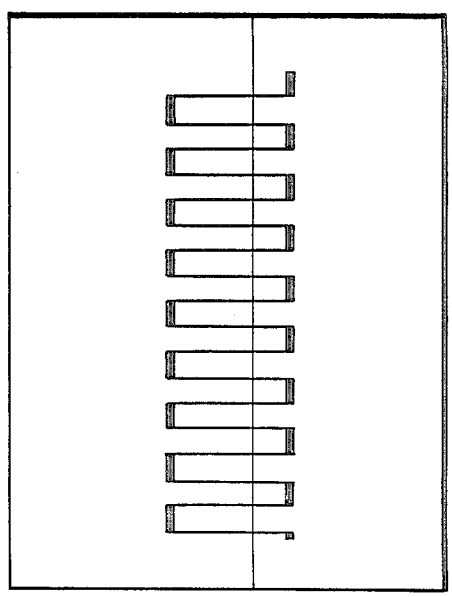

Stage 214 contains an oscillator having a frequency of approximately 300 hertz. The output of the oscillator is converted to digital logic voltages and is counted down by a flip-flop, thereby producing a sixth signal having the waveform shown in FIG. 14. The sixth signal has a duty cycle of fifty percent and a frequency of approximately 150 hertz.

Figure 15:
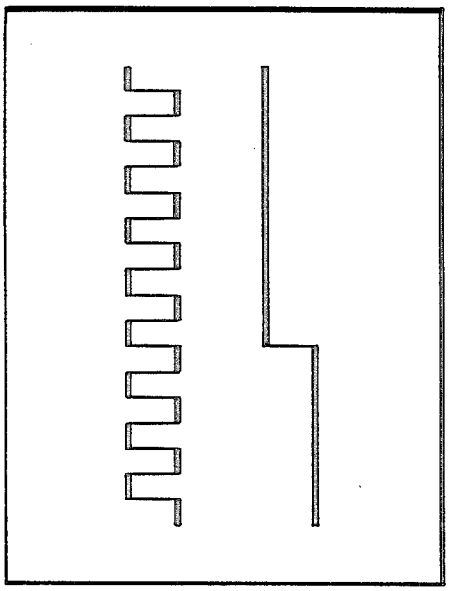
Figure 16:
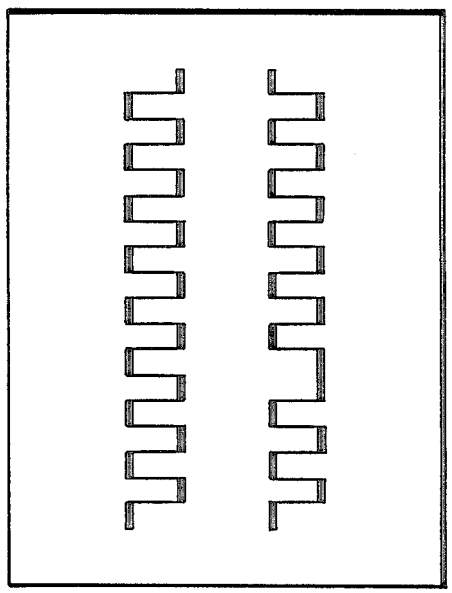

The fifth and sixth signals are then supplied to stage 216 wherein they are synchronized as shown in FIG. 15 and gated in such manner as to provide sixth and eighth signals [having respective waveforms shown in FIG. 16] at a frequency of approximately 150 hertz across the two parallel connected liquid crystal displays 130 and 132. The sixth and eighth signals are out of phase when bubbles are present in the fluid and are in phase when bubbles are absent. The crystal films are opaque when bubbles are absent and are transparent when bubbles are present. The crystal films are applied over a white or silver substrate, and to the eye of an observer, the visual effect is similar to that experienced when an observer examines a mechanical sight glass permanently installed in the conduit. Stage 220 produces the various voltages and power control required for proper electrical operation.

The oscillator stage 202 employs an operational amplifier 16 with a positive feedback loop including a high pass filter formed by capacitor 18 and resistor 20 and a low pass filter formed by resistor 20 and capacitor 22. These filters are in series, the bottom frequency of the high pass filter being essentially the same as the top frequency of the low pass filter. These frequencies are essentially the same as the resonant frequency of the transducer and prevent oscillation in undesired modes. Resistor 24 is used to set the operating bias point of the amplifier 16. Diodes 30 and 32 set the range of the amplitude of the oscillations and the range of the amplitude excursion of the transducer. Capacitor 34 determines the drive level to the transducer, and, to some extent, the phase, while resistors 26 and 28 control the maximum loop gain.

The first signal is supplied to the next stage 204 wherein it causes current to be drawn from ground through diode 38 and feeds it to capacitor 42 via diode 36. Resistor 40 provides a discharge path whereby an alternating current signal component proportional to the oscillator amplitude variations caused by bubbles is produced and is superimposed upon an unwanted direct current component. This unwanted component is removed by a high pass filter formed by capacitor 44 and resistor 46 and the alternating current component is supplied to an input of operational amplifier 48.

The second signal appears at the output of amplifier 48 and is supplied to gain control rheostat 50 of stage 206. This stage produces, with variable gain, the third signal. The third signal is supplied to stage 208. Stage 208 has a fixed gain portion constituted by resistors 58 and 62 and operational amplifier 60 and a low pass filter portion formed by resistor 62 and capacitor 64. The fourth signal appears at the output of amplifier 60.

The fourth signal is supplied to stage 210 which is a variable gain buffer state and yields across direct current blocking capacitor a signal which drives an audio device such as head phones. The fourth signal is also supplied to operational amplifier 78 of stage 214 via resistor 74. Resistors 76, 80 and 84, with the addition of diode 82, comprise a hysteresis network that supplies positive and negative threshold levels to be crossed by the fourth signal. These levels are not symetrical, the positive level having an offset that is twice the amplitude of the negative level offset. These offsets are selected to bias the resulting duty cycle, thereby providing a more realistic visual display. When bubbles are present, the fourth signal increases in the positive direction, and, if large enough, crosses the positive threshold, causing the output of amplifier 78 to attain its most negative value. As the bubbles pass away from the transducer, the fourth signal becomes more negative, and, as it passes the negative threshold level, the amplifier output swings to the most positive voltage that can be attained. The output signal of amplifier 78 then passes through capacitor 86 and resistor 88 past clamping diodes 90 and 92 and becomes the fifth signal. Resistor 94 causes the fifth signal to have a high value when no bubbles are present.

Stage 214 generates a low frequency clock voltage having the shape of a square wave at a frequency of approximately 150 hertz which is limited in amplitude by clamping diodes 110 and 112. Flip-flop 114 responds to each positive and negative going portion of the clock voltage to produce the sixth signal.

The fifth and sixth signals are supplied to flip-flop 116 of stage 216, causing it to generate a variable duty cycle seventh signal which is synchronous with the sixth signal. This variable signal has positive and negative portions that start and end at a time which is coincident with the rising edges of a sixth signal clock pulse. This variable signal is supplied to exclusive OR gate 118 together with the sixth signal. The output of gate 118 is close to synchronous with the sixth signal but is either in phase or in phase opposition therewith, depending upon the absence or presence of bubbles in the fluid, the phase transitions always taking place at the leading edges of the sixth signal. The output of gate 118 is applied to one side of the display devices 130 and 132. The sixth signal is also passed through gates 120 and 122 to the other side of these devices. Gates 120 and 122 provide a delay essentially equal to the delay of flip-flop 116 and gate 118 so that the signals applied to the two sides of the display devices are essentially synchronous. Capacitor 126 and resistor 128 block and shunt direct current to protect the devices therefrom.

All of the operational amplifiers can be identical, but have been given different identification numbers to facilitate the description of the circuitry.

While the fundamental novel features of the invention have been described and pointed out, it will be understood that various substitutions and changes in the form of the details of the embodiments shown may be made by those skilled in the art without departing from the concepts of the invention as limited only by the scope of the claims which follow.

What is claimed is:

1. Electronic apparatus adapted for use with a conduit through which a fluid flows, the fluid having a first bubble free state and a second and alternative bubble containing state, said apparatus comprising:

an oscillator employing a single piezo-electric transducer as a frequency determining element, the transducer having different frequency modes of operation enabling the transducer to resonate at different frequencies, the oscillator having a positive feedback loop containing in series a high pass filter and a low pass filter which together determine one selected mode of operation and eliminate any other transducer frequency mode, the transducer, when unloaded and operating in the selected mode, having a resonant frequency which determines the oscillation frequency and having a predetermined maximum level of amplitude excursion, the transducer, when loaded by being moved into engagement with the conduit, exhibiting a change in resonant frequency and a change in the level of amplitude excursion while remaining in the selected mode, the amount of oscillator frequency change and the amount of change in excursion level having respective values when the fluid is in the first state which differ from the respective values when the fluid is in the second state;

first means responsive to the changing amplitude values to produce an output signal when a selected one of the states is detected; and second means adjustable to different sizes of conduit to detachably clamp the transducer to the conduit.

2. Electronic apparatus adapted for use with a conduit through which a fluid flows, the fluid having a first bubble free state and an second and alternate bubble containing state, said apparatus comprising:

an oscillator employing a flat piezo-electric transducer as a frequency determining element, the transducer having axial and radial modes of excitation which have different resonant frequencies, the oscillator having a positive feedback loop containing in series a high pass filter and a low pass filter which together determine one selected radial mode of excitation for the transducer together with an associated resonant frequency and prevent the transducer from being excited in an axial mode of excitation, the transducer, when unloaded and operating in the selected radial mode wherein its amplitude elongations and contractions take place in the plane of the transducer, having a resonant frequency which determines the oscillation frequency and having a pretermined maximum level of amplitude excursion, the transducer, when loaded by being moved until one flat surface of the transducer is in engagement with the conduit, exhibiting a change in resonant frequency and a change in the level of amplitude excursion while remaining in the selected radial mode, the amount of oscillator frequency change and the amount of change in excursion level having respective values when the fluid is in the first state which differ from the respective values when the fluid is in the second state;

first means responsive to the changing amplitude values to produce an output signal when a selected one of the states is detected;

second means self adjusting to different sizes of conduit to detachably clamp the transducer to the conduit; and third means responsive to the output signal to produce a visual equivalent of said signal.

3. The apparatus of claim 1 wherein the second means includes a flat electrically non-conductive plate having first and second opposite surfaces, the transducer being disposed in fixed position adjacent the first surface, and further includes a clamp plate pivotally secured to the second surface and adapted to removably hold the conduit in fixed position adjacent the second surface with the transducer being centered upon the conduit.

4. Apparatus of claim 2 wherein said second means automatically centers the conduit with respect to the transducer in such manner that the transducer is disposed adjacent the center of the conduit.

5. Apparatus of claim 4 wherein the second means includes a hollow container having a wall with an inner surface and an outer surface, the transducer being disposed adjacent the inner surface of the wall, the conduit being disposed adjacent the outer surface of the wall.

6. Apparatus of claim 5 wherein the third means includes at least one liquid crystal display.

7. Apparatus of claim 2 wherein the first means includes means to produce a first signal at oscillator frequency which in the presence of bubbles in the fluid flow is amplitude modulated by the amplitude excursions of the transducer, means responsive to said first signal to produce said output signal, the output signal having a frequency which is proportional to the number and size of the bubbles in the fluid, said frequency having a zero value when bubbles are not present.

8. Apparatus of claim 6 wherein the display has first and second input connections, first and second signals of like phase being supplied to the corresponding input connections when bubbles are not present, first and second signals of opposite phase being supplied to the corresponding input connections when bubbles are present.

9. The combination as set forth in claim 3 wherein the plate clamp is spring loaded to prevent slippage of the conduit on the surface.

10. The combination set forth in claim 9 wherein the spring loading also enhances the acoutical contact between the transducer and the conduit.

* * * * *